United States Patent [19]

Findeisen et al.

[11] 4,310,692

[45] Jan. 12, 1982

[54] PROCESS FOR THE PREPARATION OF ALKYL-UREAS

[75] Inventors: Kurt Findeisen, Odenthal; Reinhard Freimuth, Munich; Kuno Wagner, Leverkusen, all of Fed. Rep. of Germany

[73] Assignee: Bayer Aktiengesellschaft, Leverkusen, Fed. Rep. of Germany

[21] Appl. No.: 186,355

[22] Filed: Sep. 11, 1980

[30] Foreign Application Priority Data

Sep. 14, 1979 [DE] Fed. Rep. of Germany ....... 2937331

[51] Int. Cl.³ .......................................... C07C 127/15
[52] U.S. Cl. ........................................ 564/61; 564/58
[58] Field of Search ................................... 564/58, 61

[56] References Cited

U.S. PATENT DOCUMENTS

| 1,785,730 | 12/1930 | Davis | 564/61 |
|---|---|---|---|
| 2,145,242 | 1/1939 | Arnold | 564/61 |
| 2,253,528 | 8/1941 | Olin | 260/553 |
| 2,257,717 | 9/1941 | Olin | 564/61 |
| 2,611,782 | 9/1952 | Bortnick | 564/58 X |
| 3,937,727 | 2/1976 | Throckmorton et al. | 260/553 |

FOREIGN PATENT DOCUMENTS

| 855551 | 7/1951 | Fed. Rep. of Germany . | |
|---|---|---|---|
| 896640 | 10/1953 | Fed. Rep. of Germany . | |
| 1111612 | 7/1961 | Fed. Rep. of Germany | 564/58 |
| 1111613 | 7/1961 | Fed. Rep. of Germany . | |
| 55003 | 4/1967 | German Democratic Rep. | 564/58 |

OTHER PUBLICATIONS

J. Russ. Phys. Chem. Soc. 37 1.
Houben-Weyl Georg Thieme Verlog, Stuttgart, 1952, vol. VIII 153.

Primary Examiner—John Doll
Attorney, Agent, or Firm—Gene Harsh; Joseph C. Gil; Lyndanne M. Whalen

[57] ABSTRACT

The instant invention is directed to a process for the preparation of an alkyl-substituted urea of the formula

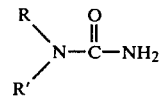

wherein R and R', which may be the same or different, represents hydrogen or a saturated hydrocarbon radical, provided that at least one represents a saturated aliphatic hydrocarbon radical, comprising reacting, unpressurized, at from 110° to 170° C., urea with an amine having a boiling point, under normal pressure, at least 10° C. below the reaction temperature, said amine corresponding to the formula:

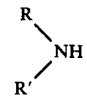

wherein R and R' are as defined above, and wherein for each mol of urea present, at least one mol of amine is used, the improvement wherein the reaction is carried out in the presence of from 20 to 95% by weight, based on the total quantity of reactants and auxiliary agents, if any, of an organic liquid boiling, under normal pressure, above the reaction temperature, which is inert under the reaction conditions and which serves as a dispersing agent or a solvent for the urea and for the product of the process and is a solvent for the amine.

4 Claims, No Drawings

PROCESS FOR THE PREPARATION OF ALKYL-UREAS

BACKGROUND OF THE INVENTION

This invention relates to a process for the preparation of alkyl-ureas by the direct reaction of alkyl-amines with urea.

N-alkyl- and N,N-dialkyl-ureas, particularly N,N-dimethyl- and N,N-diethyl-urea are known. These compounds provide particularly interesting precursors and intermediate products for the production of isocyanates, active substances, polyurethanes and rocket propellants (as N,N-dimethylhydrazine, J. Russ. Phys. Chem Soc. 37 1).

Various preparations, such as a reaction of an appropriate carbamic acid chloride with ammonia, the reaction of a salt of an appropriate amine with an alkali metal cyanate or the reaction of an appropriate amine with a nitro-urea, have been suggested (Houben-Weyl, Georg Thieme Verlag, Stuttgart 1952, Volume VIII, 153). The starting materials used are relatively expensive, physiologically hazardous and difficult to obtain. Preparation by the reaction of an alkyl- or diaklyl-amine with urea has also been attempted. In U.S. Pat. No. 2,253,528, the process is either carried out in a closed reaction vessel under excess pressure or, if the boiling point of the amine is the same as or higher than the reaction temperature, it is carried out in an open system. It has also been suggested that the reaction be carried out in a complex countercurrent apparatus under pressure as far as possible (German Auslegeschrift No. 1,111,613). Alternatively, it has been proposed to introduce a gaseous amine into the molten urea (German Pat. No. 896,640). Since it is known that urea, when molten, is prone to secondary reactions (e.g. biuret formation), the last mentioned prior art process suffers from the disadvantage that only impure products are obtained and in a poor yield.

According to German Pat. No. 855,551 or U.S. Pat. No. 3,937,727, the reaction between urea and methyl- or dimethyl-amine takes place under pressure in an aqueous or anhydrous medium. These known processes, which take place under external pressure, suffer from the disadvantage that autoclaves or complicated apparatus have to be used.

An object of the present invention was to provide a process which avoids the above-mentioned disadvantages of the known processes. That is, in particular, a process which, regardless of the boiling point of the amine used, allows the production, under atmospheric pressure, of unsymmetrical alkyl-ureas of high purity and in a high yield so that the industrial production of these compounds may be greatly simplified.

Surprisingly, this problem may be solved by the concomitant use of certain diluents in the preparation of unsymmetrical alkyl-ureas by the reaction of urea with aliphatic mono- or diamines. The solution according to the present invention of the prevailing problem may be said to be surprising as it was not to be expected that the concomitant use of diluents of this type would reduce the tendency of urea toward the formation of undesired secondary products.

DESCRIPTION OF THE INVENTION

The present invention relates to a process for the preparation of an alkyl-substituted urea of the formula:

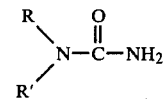

wherein
R and R', which may be the same or different, represent hydrogen or a saturated aliphatic hydrocarbon radical, provided that at least one represents a saturated aliphatic hydrocarbon radical, comprising reacting, unpressurized, at from 110° to 170° C., urea with an amine having a boiling point, under normal pressure, at least 10° C. below the reaction temperature, said amine corresponding to the formula:

wherein R and R' are as defined above, and wherein for each mol of urea present at least 1 mol of amine is used, the improvement wherein the reaction is carried out in the presence of from 20 to 95% by weight, based on the total amount of reactants and auxiliary agents, of an organic liquid boiling, under normal pressure, above the reaction temperature which is inert under the reaction conditions and which serves as a dispersing agent or solvent for the urea and for the product of the process and as a solvent for the amine.

The starting materials for the present process are amines corresponding to the following general formula:

wherein
R and R' are as defined above.

In the present process, it is preferred to use amines corresponding to the above general formula wherein R and R' each represents hydrogen or a $C_1$–$C_5$, preferably $C_1$ or $C_2$, saturated aliphatic hydrocarbon radical, provided at least one thereof represents a hydrocarbon radical of this type. The amines which are to be used in the present process have a boiling point under normal pressure which is at least 10° C. below the reaction temperature.

Examples of suitable amines include, e.g. methylamine, ethylamine, n-propylamine, n-pentylamine, dimethylamine, diethylamine, diisobutylamine and methylethylamine. Dimethylamine and diethylamine are preferred for use in the present process.

The process according to the present invention is carried out in the presence of diluents. These diluents comprise organic liquids which are inert under the conditions of the present process which have a boiling point, under normal pressure, above the reaction temperature and which serve as a solvent or dispersing agent for the urea of the product of the process and serve as a solvent for the amine. Examples of suitable diluents include: chlorobenzene, dichlorobenzenes, trichlorobenzenes, toluene, xylenes (such as o-xylene, p-xylene or commercial xylene mixtures), sulfolane, benzonitrile, nitrobenzene, N-methyl-pyrrolidone and diethylene glycol-monomethyl ether. Dichlorobenzenes, N-methyl-pyrrolidone or diethylene glycol-monomethyl ether are examples of particularly preferred diluents.

In carrying out the present process, the starting materials are used in such amounts that at least 1 mol, preferably from 1 to 2 mols, of amine are reacted per mol of urea. The diluent is introduced in a quantity of from 20 to 95%, preferably from 40 to 85%, by weight, based on the total quantity of the reactants and auxiliary agents.

The present process is carried out at from 110° to 170° C., preferably from 115° to 150° C., more preferably from 120° to 135° C., no external pressure being applied so that the resulting ammonia may escape at any time.

In order to carry out the present process, the amine, which may be dissolved in a diluent, is introduced into a solution or dispersion of the urea in the diluent, heated to the reaction temperature. The course of the reaction may be followed by the quantity of the ammonia which results spontaneously. After the reaction, the product may be obtained from the reaction mixture by crystallization or, after removing the diluent, by distillation.

The present process allows the preparation of unsymmetrical alkyl- or dialkyl-ureas in a particularly simple way, for which, up until now, no technically completely satisfactory means has been known.

In the following Examples, all of the percentages relate to percent by weight.

EXAMPLES

EXAMPLE 1

1.2 kg (20 mols) of urea are suspended in 2.5 liters dry o-dichlorobenzene. This is heated to an internal temperature of 135° C. and a stream of dimethylamine is slowly introduced. When the reaction temperature has been reached, more dimethylamine is added, with cooling, until 1.08 kg (24 mols) have been introduced. The reaction product which crystallizes after cooling to room temperature is separated by suction filtration and washed using 1 liter of o-dichlorobenzene and 2 liters of alcohol. 1550 g (88% of the theoretical yield) of N,N-dimethyl-urea having a melting point of 182°–183° C. are obtained. By isolating the product dissolved in the mother liquor, after evaporation of the mother liquor, the yield may be increased to 97%.

EXAMPLE 2

180 g (3 mols) of urea are suspended in 500 ml of dry xylene. This is heated to an internal temperature of from 130° to 135° C. and a solution of 219 g (3 mols) of diethylamine in 250 ml of xylene is slowly introduced. When the reaction temperature has been reached, more dimethylamine solution is added, with stirring. When all of the amine solution has been added, the reaction mixture is concentrated to half its volume. It is then left to cool to room temperature and the crystallized reaction product is separated by suction filtration. 290 g (83% of the theoretical yield) of N,N-diethyl-urea having a melting point of 67° C. are obtained.

EXAMPLE 3

180 g (3 mols) of urea are suspended in 500 ml of dry xylene. This is heated to an internal temperature of from 130° to 135° C. and a mixture of 303 g (3 mols) of dipropylamine and 250 ml of xylene is slowly introduced. When the reaction temperature has been reached, more dipropylamine mixture is added, with stirring. When all of the amine solution has been added, the reaction mixture is concentrated to half its volume. It is then left to cool to room temperature and the crystallized reaction product is separated by suction filtration. 345 g (80% of the theoretical yield) of N,N-dipropyl-urea having a melting point of 69° C. are obtained.

EXAMPLE 4

120 g (2 mols) of urea are suspended in 400 ml of dry xylene. This is heated to an internal temperature of from 120° to 125° C. and a stream of methylamine is slowly introduced. When the reaction temperature has been reached, more methylamine is added, with stirring, until 120 g (3.9 mols) have been introduced. The reaction product is separated from the cooled solution and washed using 100 ml of xylene. 117 g (79% of the theoretical yield) of methyl-urea having a melting point of 96° C. are obtained.

EXAMPLE 5

120 g (2 mols) of urea are suspended in 500 ml of dry xylene. This is heated to an internal temperature of from 120° to 125° C. and a stream of ethylamine is slowly introduced. When the reaction temperature has been reached, more ethylamine is added, with stirring, until 125 g (2.75 mols) have been introduced. The reaction product, after it has been concentrated slightly under vacuum, is separated from the cooled solution by suction filtration and washed using a little cold xylene. 147 g (83% of the theoretical yield) ethyl-urea having a melting point of 86° C. are obtained.

EXAMPLE 6

120 g (2 mols) of urea are suspended in 350 ml of dry xylene. This is heated to an internal temperature of from 120° to 125° C. and a mixture of 120 g (2.05 mols) of propylamine and 200 ml of xylene are slowly introduced. When the reaction temperature has been reached, more propylamine mixture is added, with stirring. When all of the amine has been added, the reaction mixture is concentrated to half its volume. This is then left to cool to room temperature, the crystallized reaction product being filtered off and washed using a little cold xylene. 165 g (81% of the theoretical yield) of propyl-urea having a melting point of 101° C. are obtained.

EXAMPLE 7

120 g (2 mols) of urea are suspended in 350 ml of dry xylene. This is heated to an internal temperature of from 120° to 125° C. and a mixture of 175 g (2 mols) of n-amylamine and 200 ml of xylene is slowly introduced. When the reaction temperature has been reached, more amylamine mixture is added, with stirring. When all of the amine has been added, the reaction mixture is concentrated to half its volume. This is then left to cool to room temperature, the crystallized reaction product being filtered off and washed using a little cold xylene. 229 g (88% of the theoretical yield) of n-amylurea having a melting point of 94° C. are obtained.

What is claimed is:

1. In a process for the preparation of an alkyl-substituted urea of the formula:

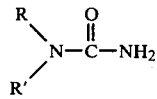

wherein R and R', which may be the same or different, represent hydrogen or a saturated hydrocarbon radical, provided that at least one represents a saturated aliphatic hydrocarbon radical, comprising reacting unpressurized, at from 110° to 170° C., urea with an amine having a boiling point, under normal pressure, at least 10° C. below the reaction temperature, said amine corresponding to the formula:

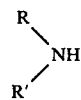

wherein R and R' are as defined above, and wherein for each mol of urea present, at least one mol of amine is used, the improvement wherein the reaction is carried out in the presence of from 20 to 95% by weight, based on the total quantity of reactants and auxiliary agents, if any, of an organic liquid boiling, under normal pressure, above the reaction temperature, which is inert under the reaction conditions and which serves as a dispersing agent or a solvent for the urea and for the product of the process and is a solvent for the amine.

2. The process of claim 1, wherein said amine is dimethylamine or diethylamine.

3. The process of claim 1, wherein said organic liquid is selected from the group consisting of dichlorobenzenes, N-methyl-pyrrolidone and diethylene glycol-monomethyl ether.

4. The process of claim 1, wherein said organic liquid is used in a quantity of from 40 to 85% by weight, based on the total quantity of reactants and auxiliary agents, if any.

* * * * *